United States Patent [19]

Albisser et al.

[11] 4,245,634

[45] Jan. 20, 1981

[54] ARTIFICIAL BETA CELL

[75] Inventors: Anthony M. Albisser, Toronto; Bernard S. Leibel, Newmarket, both of Canada

[73] Assignee: Hospital for Sick Children, Toronto, Canada

[21] Appl. No.: 11,601

[22] Filed: Feb. 12, 1979

Related U.S. Application Data

[63] Continuation of Ser. No. 764,270, Jan. 31, 1977, abandoned, which is a continuation-in-part of Ser. No. 639,948, Dec. 11, 1975, abandoned.

[51] Int. Cl.$^3$ .............................................. A61J 7/00
[52] U.S. Cl. .................................. 128/213 R; 128/260
[58] Field of Search ................... 128/635, 637, 213 R, 128/214 E, 214 F, 260

[56] References Cited

U.S. PATENT DOCUMENTS

| | | | |
|---|---|---|---|
| 3,809,871 | 5/1974 | Howard et al. | 128/214 E |
| 3,837,339 | 9/1974 | Aisenberg et al. | 128/213 R |
| 3,946,731 | 3/1976 | Lichtenstein | 128/214 E |
| 4,003,379 | 1/1977 | Ellinwood, Jr. | 128/260 |
| 4,055,175 | 10/1977 | Clemens et al. | 128/213 R |

OTHER PUBLICATIONS

Pagurer et al., "Medical & Biological Engineering," vol. 10, No. 6, Nov. 1972, pp. 752–761.
Cahil, Jr. et al., "Diabetes," vol. 21, Supplement 2, 1972, pp. 703–712.

*Primary Examiner*—William E. Kamm
*Attorney, Agent, or Firm*—Hirons, Rogers & Scott

[57] ABSTRACT

An artificial beta cell regulates blood glucose concentration in a subject by continuously analyzing blood from the patient and deriving a computer output signal to drive a pump which infuses insulin at a rate corresponding to the signal. A value of blood glucose concentration from the analyzed blood is used by a computer to determine a rate of change of this concentration which in turn is used to derive a projected blood glucose level. A sigmoidal relationship between the projected blood glucose concentration and the rate of infusion is used to determine the actual rate of infusion required and hence an output signal is fed to the pump to create this actual rate of insulin infusion.

1 Claim, 21 Drawing Figures

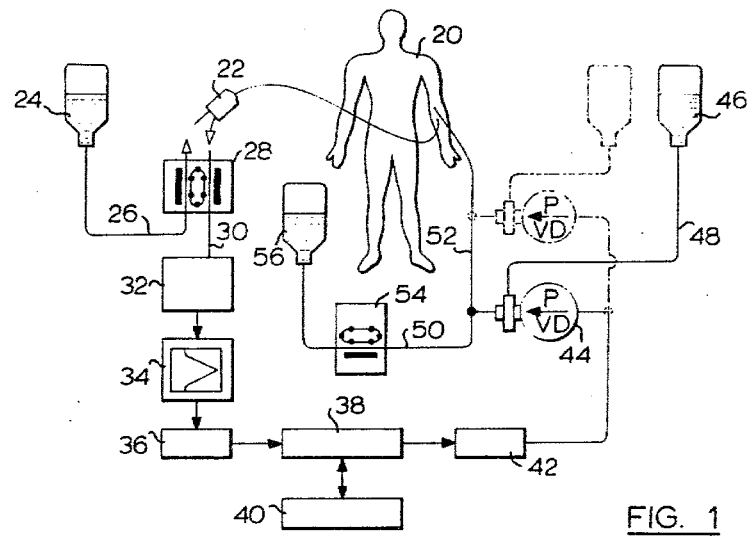
FIG. 1
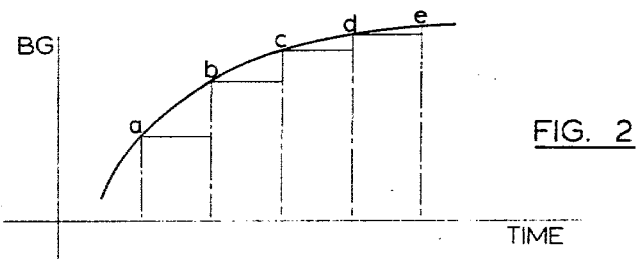
FIG. 2
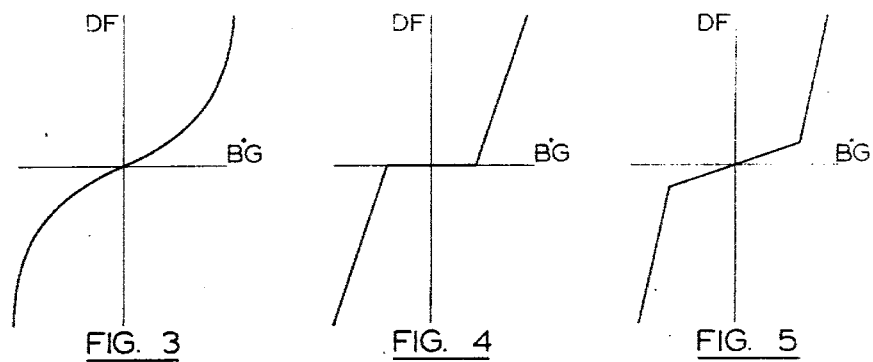
FIG. 3
FIG. 4
FIG. 5

ARTIFICIAL BETA CELL

This application is a Continuation of United States Patent Application Ser. No. 764,270, filed Jan. 31, 1977 now abandoned; which is a Continuation-In-Part of application Ser. No. 639,948, Dec. 11, 1975, abandoned.

This invention relates to an artificial beta cell for use primarily in controlling blood glucose levels in diabetic subjects.

The beta cells in the pancreas produce a powerful hormone known as insulin which is essential to the control of glucose concentration in the blood. Failure to produce insulin in appropriate quantities results in the onset of diabetes mellitus and people suffering from this disease are referred to as "diabetics". This disease is characterized by hyperglycaemia and death can result from ketoacidosis.

Insulin was first administered to a diabetic boy in 1922 with dramatic results. It was first thought that insulin injections were the complete answer to diabetes but it was later found that the insulin treatment does not remove the probability of blindness or kidney failure or other microvascular complications from a diabetic's prognosis.

Although diabetes mellitus is not fully understood, it is generally accepted that the best insurance against these complications would be to control blood glucose at an optimal level. At present, a variety of different insulin injections are available for the treatment of diabetes. Some patients are better managed with short acting insulin which requires several injections per day but gives a degree of flexibility to vary exercise and food. Other patients are better managed with one of the longer acting forms of insulin which require less frequent injections. Although these longer acting insulins were at first thought to be particularly advantageous, they have in fact caused undesirable side effects in some patients. Neither the short nor the long acting varieties of insulin are capable of regulating a patient's blood glucose concentration accurately on a minute to minute basis because of varying demands created by food and exercise. Consequently, the patient must follow a life of balanced diet and exercise to prevent sudden and excessive changes in the requirements for insulin. Such a regimen will maintain his blood glucose concentration below an acceptable upper limit, thereby limiting the possibility of hyperglycaemia, and above a safe lower limit thereby limiting the possibility of hypoglycaemia. Unfortunately a dangerously low blood glucose concentration can also result from the use of larger infusions of insulin to counteract a rising concentration of blood glucose. This is because there is an overshoot when the concentration of blood glucose ceases to increase or actually decreases and the presence of the insulin causes a rapid decline in blood glucose concentration to a concentration below the safe limit. The resulting hypoglycaemia can be fatal in some cases.

Because of the shortcomings of the treatment using insulin in periodic doses, attention has been turned to the creation of an artificial beta cell which would continuously monitor a patient's need for insulin and satisfy that need by administering insulin to the patient. One approach has been to continuously monitor a patient's blood glucose concentration and to regulate this concentration by administering insulin when the concentration reaches an upper limit, and to administer dextrose when the blood glucose concentration reaches a lower limit. This approach (referred to as limit regulation) has severe difficulties because it is possible to overshoot both the upper and lower limits. It will be apparent from the foregoing that any attempt to use large doses of insulin to prevent or limit sudden surges in blood glucose concentration past the upper limit can result in hypoglycaemia. Dextrose must then be administered to prevent a drop in concentration below the lower limit. For these reasons, the system is not capable of controlling sudden changes in blood glucose concentration. Consequently, although this approach may be better than simple periodic doses of insulin, it also requires a strict regimen in order to ensure that there are no sudden and large requirements for insulin to cause sudden overshoot beyond the limits.

A second approach to an artificial beta cell is to use a proportional regulation by matching the infusion rate of insulin to the blood glucose concentration according to a linear relationship. Here again, hypoglycaemia can result if there is a large requirement for insulin followed by a natural reduction in the blood glucose concentration. Both the aforementioned limit regulation and this linear regulation have the disadvantage that they ignore variation in blood glucose concentration during the period after the insulin administering pump has been shut off.

A third approach was developed in which a closer correlation between blood glucose concentration and a rate of insulin infusion was used. This approach was the subject of a paper delivered in Chicago, Ill., U.S.A. in June 1973 to the Annual Meeting of the American Diabetes Association and in Rochester, N.Y., U.S.A. in August 1973 to the Joint Meeting of the International Federation of Automatic Control, the American Physiological Society and the International Union of Physiological Science. An article to the same subject matter and entitled "Clinical Control of Diabetes by the Artificial Pancreas" subsequently appeared in the May 1974 edition of "Diabetes". This is the Journal of The American Diabetes Association. In the article, an artificial beta cell is described in which a patient's blood is analysed for blood sugar concentration. Values of this concentration are fed to a computer which is programmed to determine a rate of change of the blood glucose concentration, and this in turn is used to determine a projected blood glucose concentration. A sigmoidal relationship between the projected blood glucose concentration and the rate of infusion is used to determine the actual rate of insulin infusion required. This actual rate value is used to drive an insulin pump.

In this third system, the projected blood glucose concentration was derived from an equation involving a so-called "difference factor". This factor was an asymmetric exponential function of the rate of change of blood glucose concentration.

Even with the sophisticated control in this third approach, there was a requirement for a complementary dextrose infusion system to ensure that dextrose was available to limit the possibility of hypoglycaemia.

The present invention is an improvement over the third approach. A difference factor has been developed which involves the use of a function which is based on a combination cubic and linear relationship and which varies with an average rate of change of blood glucose concentration. The resulting beta cell using this difference factor is sufficiently sensitive that the corresponding dextrose infusion system previously used is no longer necessary. This significant improvement simplifies the beta cell and provides better control of a patient's insulin requirements even when surges in blood glucose concentration are experienced.

A preferred embodiment of the invention will be described with reference to the drawings in which:

FIG. 1 is a schematic view of an artificial beta cell according to the invention coupled to a diabetic subject;

FIG. 2 is a graph illustrating the use of serial readings of blood glucose concentration to determine an average rate of change of blood glucose concentration;

Figure 6:
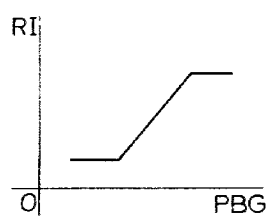
Figure 7:
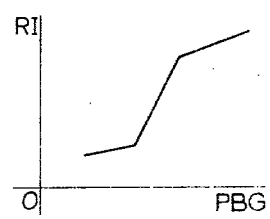
Figure 8:
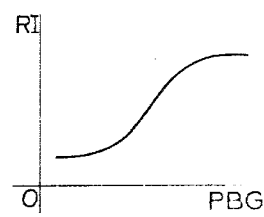
Figure 9:
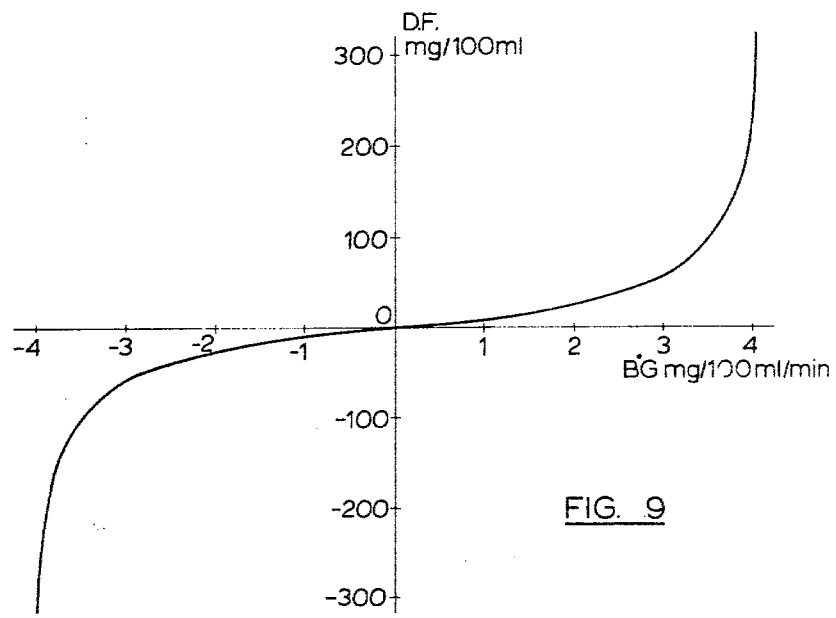
Figure 10:
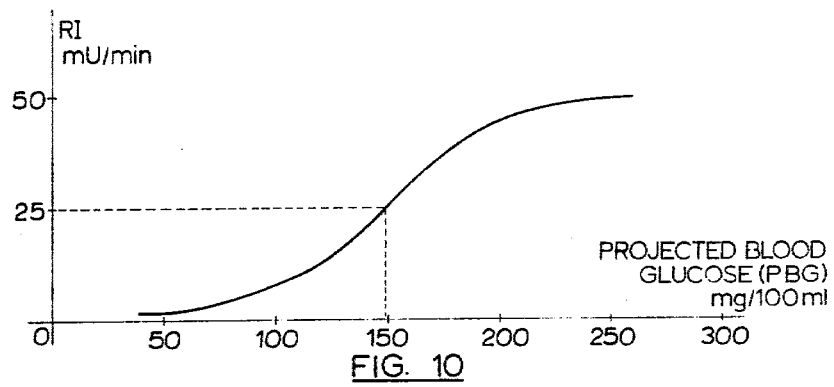
Figure 11:
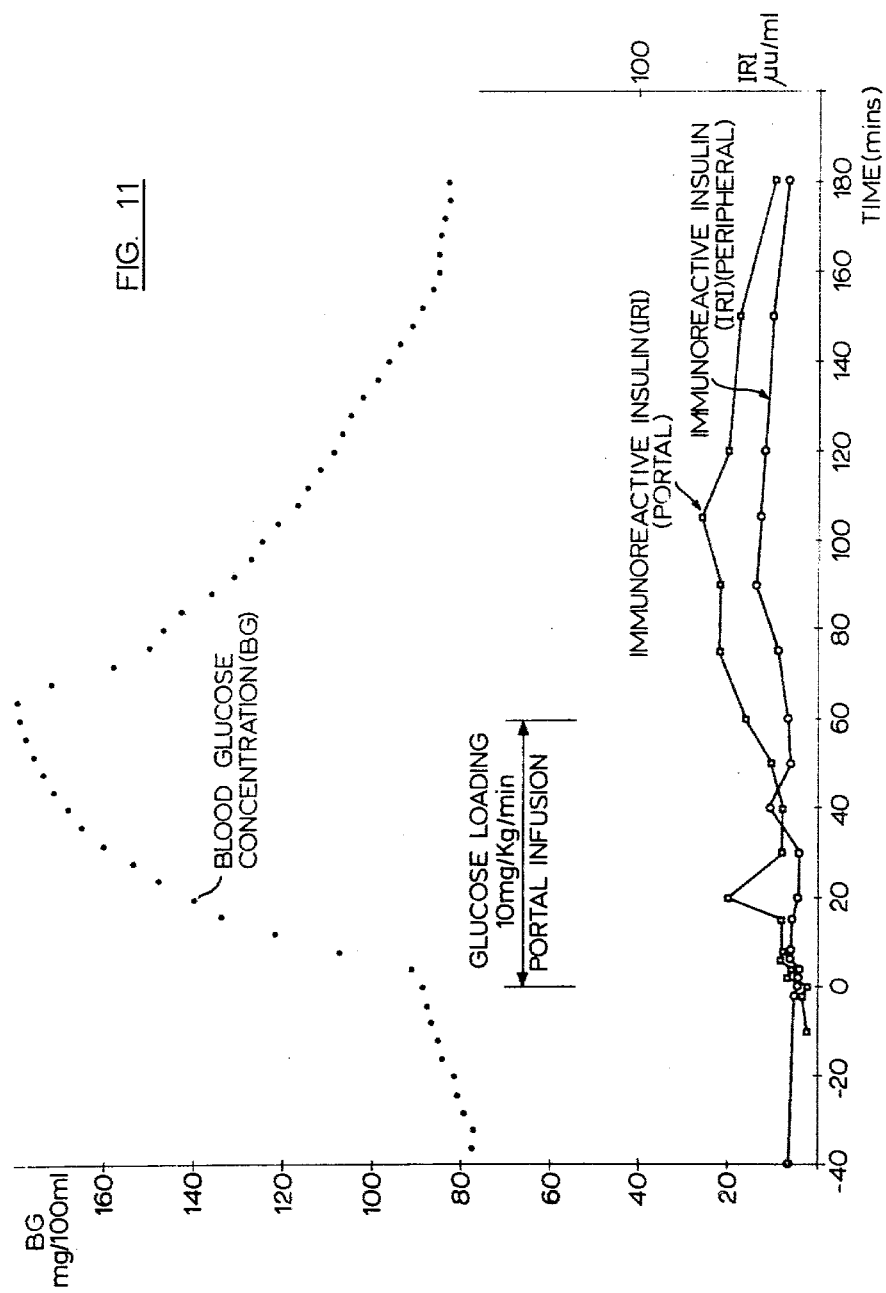
Figure 12:
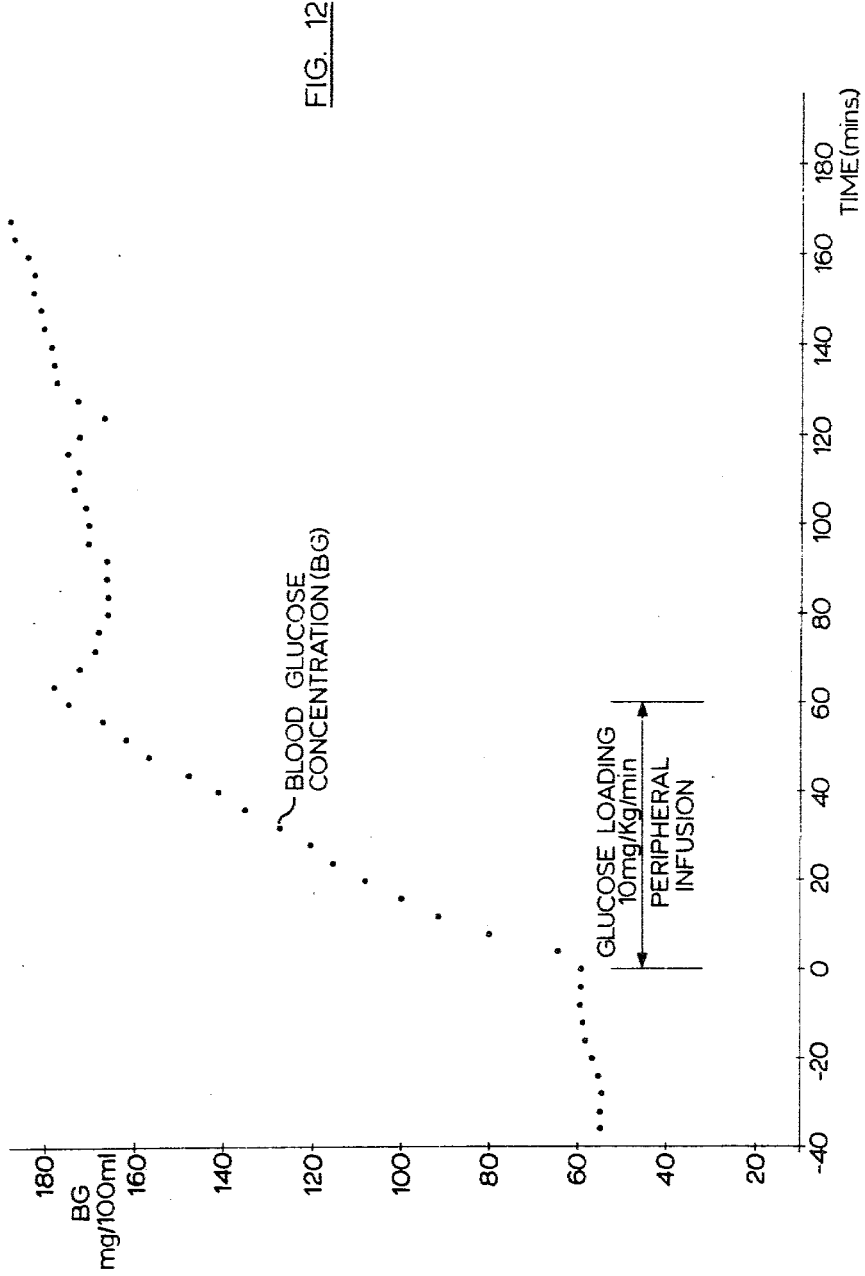
Figure 13:
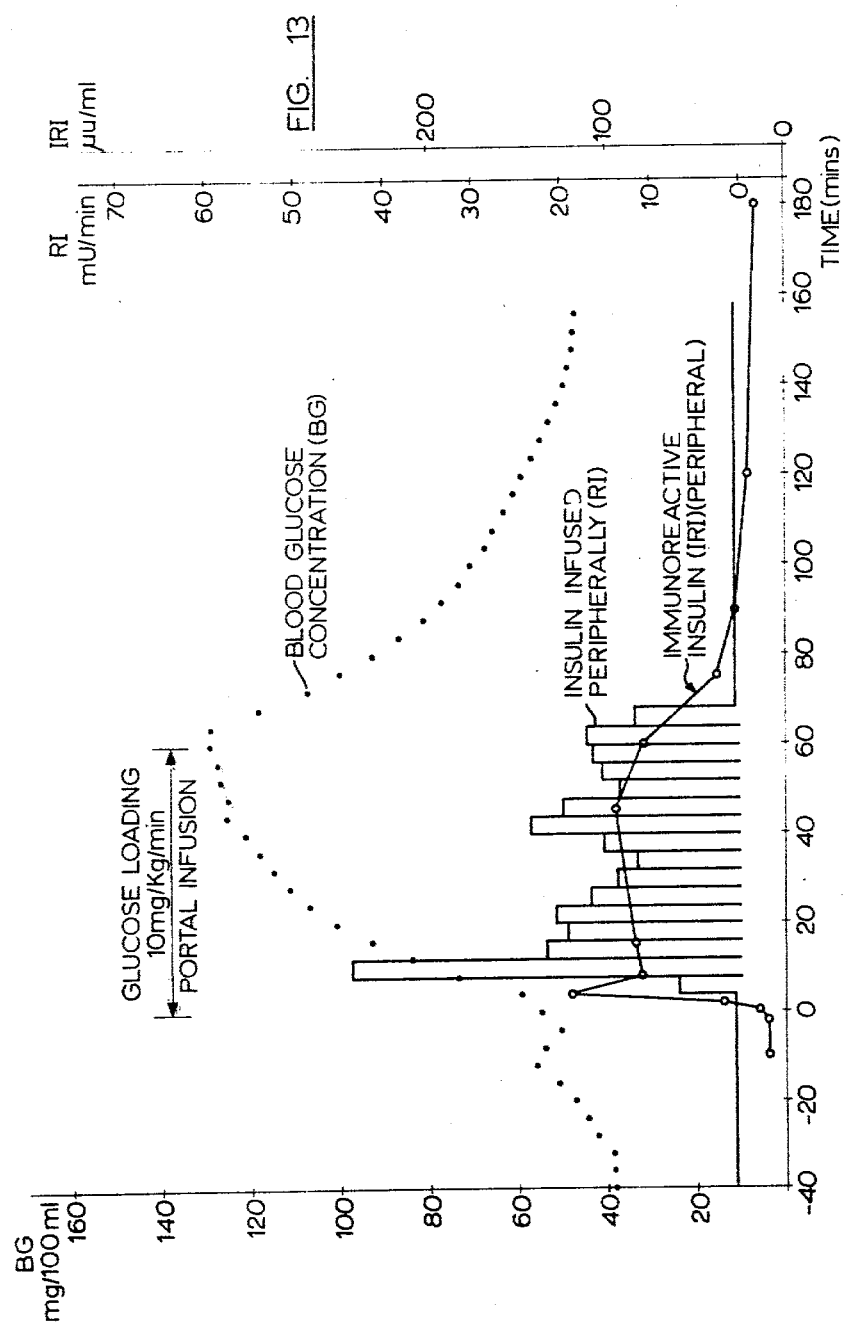
Figure 14:
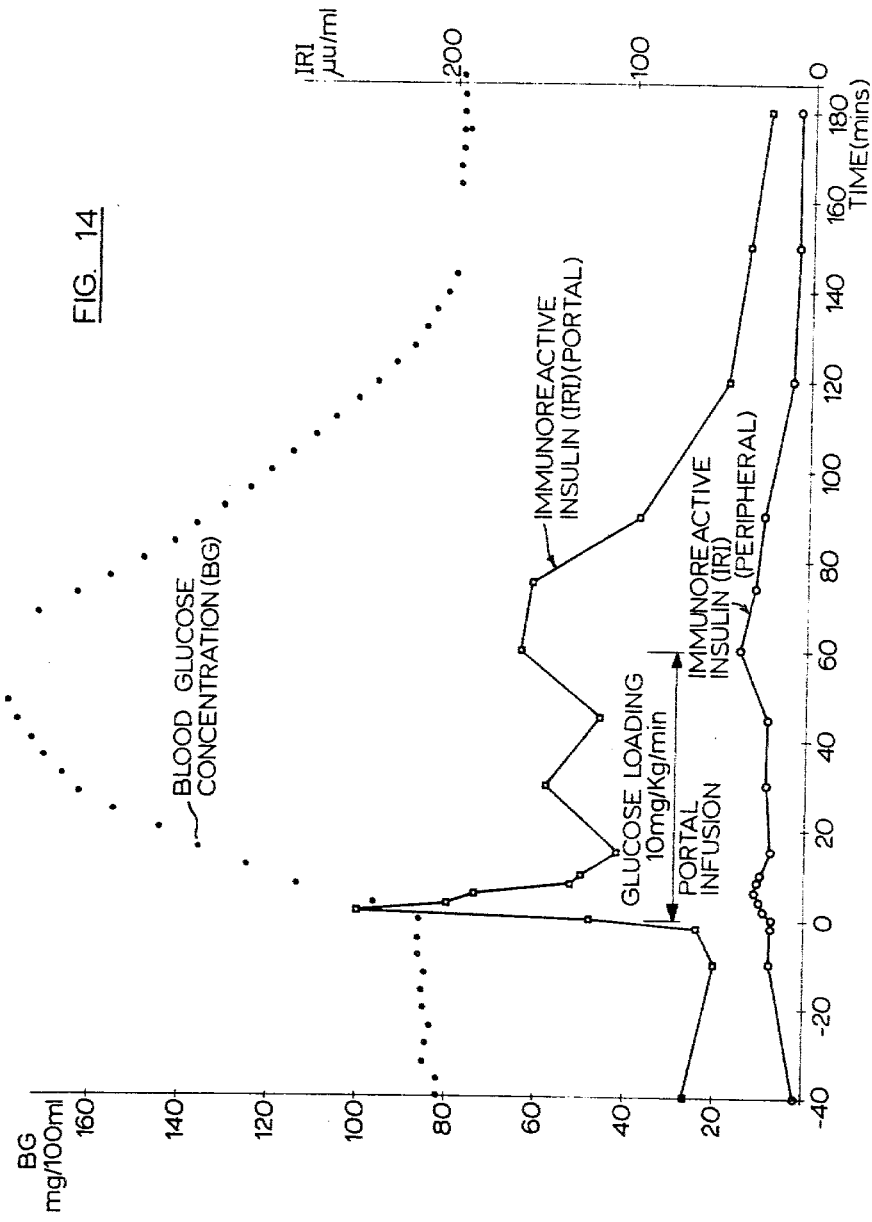
Figure 15:
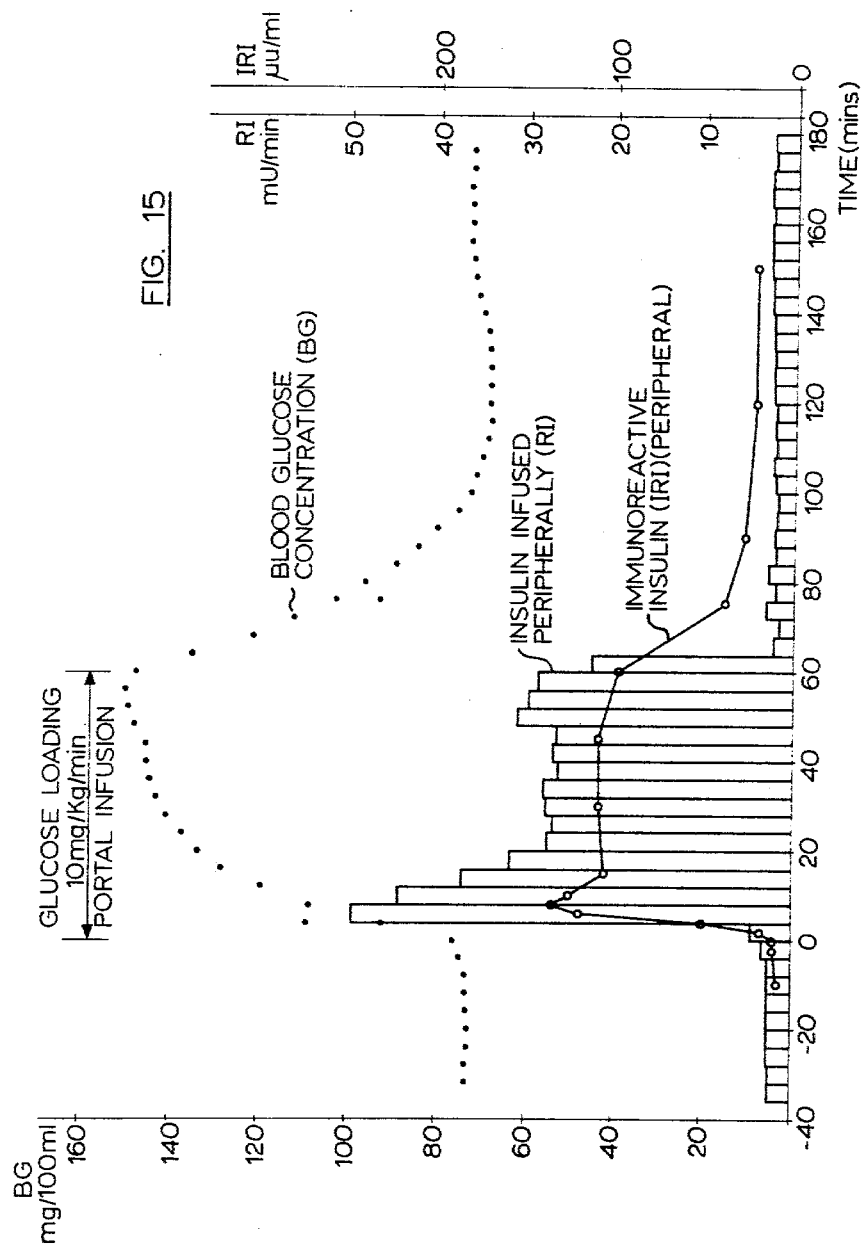
Figure 16:
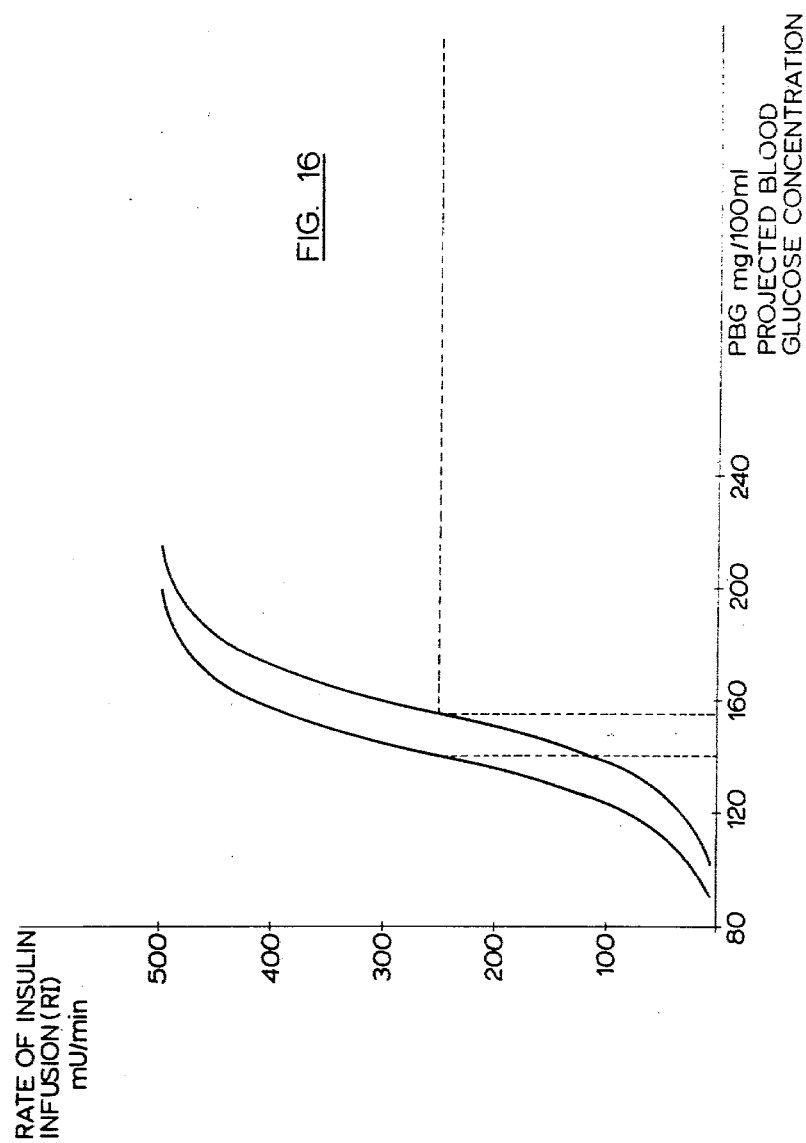
Figure 17:
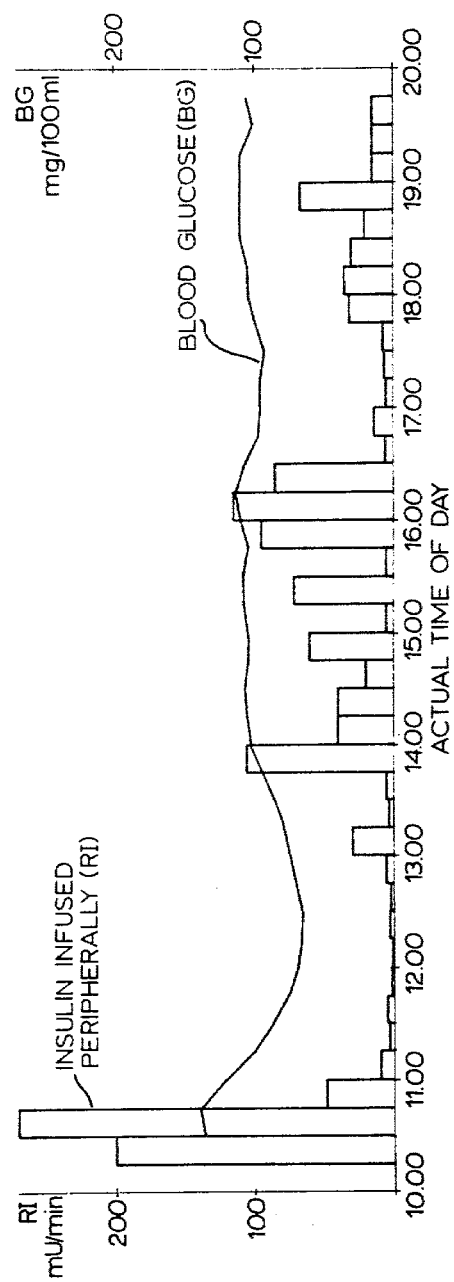
Figure 18:
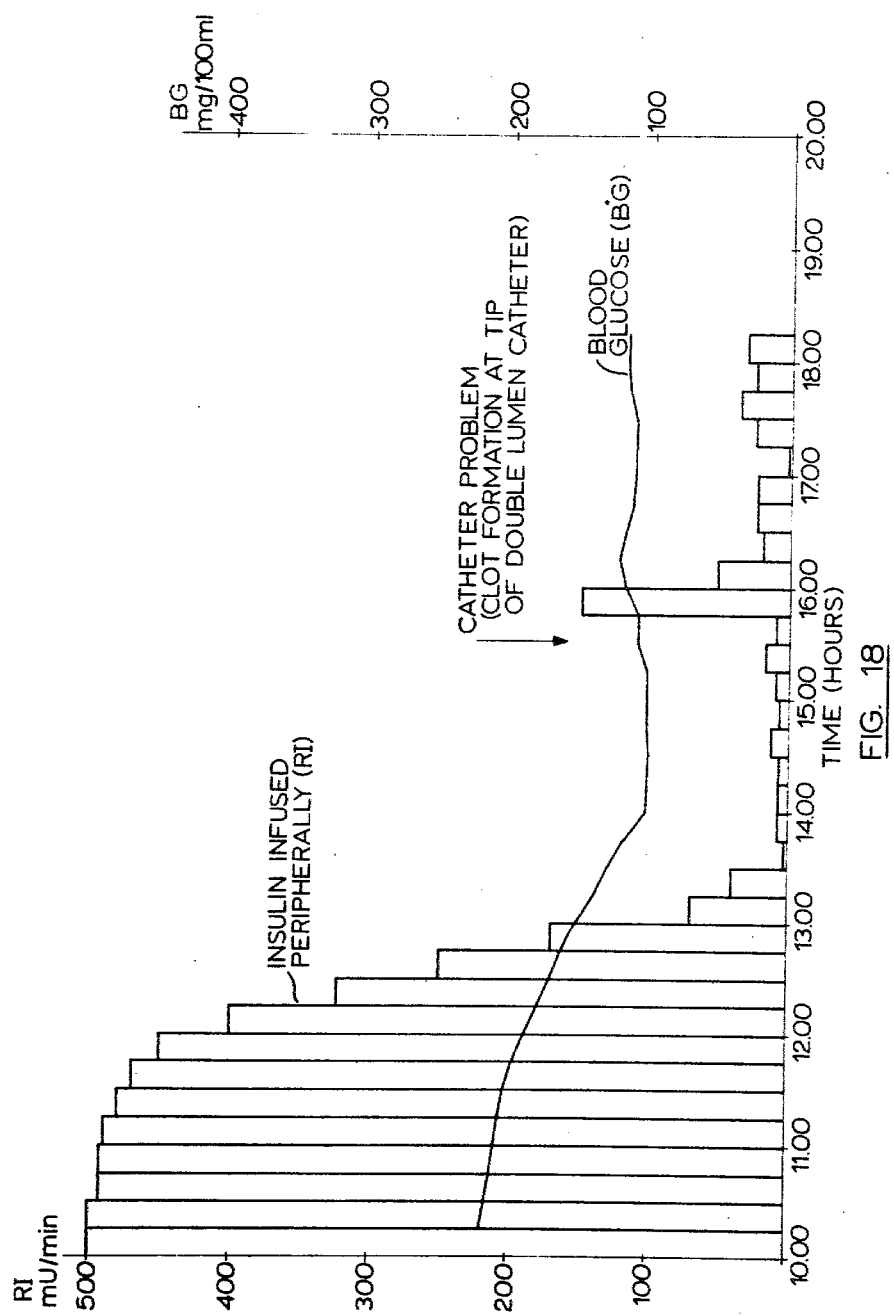
Figure 19:
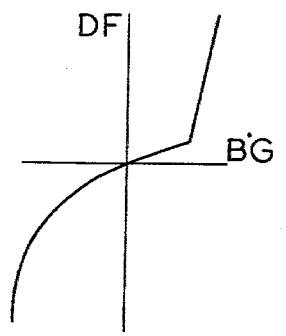
Figure 20:
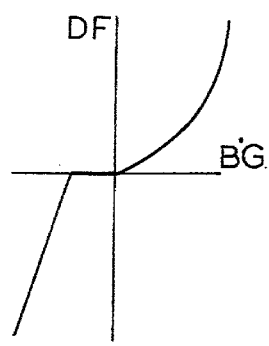
Figure 21:
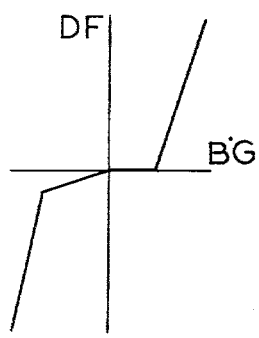

FIGS. 3, 4, and 5 are graphs showing typical curves from families of symmetrical curves used in determining a "difference factor" from the rate of change of a patient's blood glucose concentration;

FIGS. 6, 7 and 8 are graphs showing typical curves from families of sigmoidal curves used in determining a subject's insulin requirement;

FIG. 9 is an actual graph of the type shown in FIG. 3 and used in the exemplary treatment of two dogs;

FIG. 10 is an actual graph of the type shown in FIG. 6 and used in the treatment of the dogs;

FIG. 11 is a graph showing the effects of a glucose loading test on a first of the dogs;

FIG. 12 is a graph showing a glucose loading test on the same dog after pancreatectomy;

FIG. 13 is a graph showing the results obtained from a glucose loading test on the same dog when the dog is being treated using the present apparatus;

FIGS. 14 and 15 are graphs corresponding to FIGS. 11 and 13 but for the second of the two dogs;

FIG. 16 shows an actual graph of the relationship between the rate of insulin infusion and the projected blood glucose concentration in a human patient treated with the apparatus;

FIGS. 17 and 18 are graphs illustrating the results obtained when treating this patient on two separate days; and FIGS. 19 to 21 are further graphs similar to FIGS. 3 to 5.

Initially, structural aspects of a preferred embodiment of an artificial beta cell will be described with reference to FIG. 1 and then the operation of the beta cell will be described. As seen in FIG. 1, a subject 20 loses blood through a dual-lumen catheter 22 which also carries an anti-coagulent such as heparin to dilute the blood. The anti-coagulent is stored in a reservoir 24 and is pumped through a line 26 by a peristaltic pump 28 which also pumps diluted blood through a line 30 in the opposite direction. The pump runs continuously to drive the diluted blood from the line 30 into a glucose analyser 32. As the diluted blood enters the analyser it is filtered, diluted further with physiological saline solution, and then segmented with air into discrete bits to be dialyzed against a glucose oxidase-peroxidase colour reagent. The presence of blood glucose specifically alters the colour of the reagent and the optical density of the resulting colour is measured in a narrow wavelength band of about 600 nm (i.e. $600 \times 10^{-9}$ meters) in a colorimeter. The resulting optical density is then fed to a chart recorder 34 to give a visual readout and a retransmitting slide wire in the recorder feeds a corresponding signal to an analog-to-digital converter 36. This converter then prepares a computer input for a digital computer 38 which in turn prepares a computer output as will be described.

The computer 38 is programmed according to an algorithm which will be discussed later. The converter 36 feeds the digital signal corresponding to an optical density read by the glucose analyser 32 to the computer 38. By sampling the readings from the glucose analyser many times a second, the computer is able to determine the infusion rate of insulin for the subject by use of the algorithm programmed into the computer. A typewriter 40 is coupled to the computer 38 to obtain readouts and to control the computer for establishing a particular form of the algorithm for a given subject.

Once the infusion rate required by the subject has been determined, digital signals are fed from the computer 38 to a pump interface 42 which controls a pulsatile pump 44. This pump receives insulin from a reservoir 46 by way of a line 48 and feeds the insulin into a junction between further lines 50 and 52. The line 50 receives saline solution from a peristaltic pump 54 which draws the solution from a reservoir 56. Consequently, insulin from the pump 44 is mixed with the saline solution before being fed through the line 52 to the subject 20. There is therefore a closed loop which includes the subject.

Although the computer 38 has been described as a digital computer, it will be evident that the computer and converter 36 can be replaced by an analog computer although a digital computer is preferable. Similarly, the pump 44 can be driven in analog fashion rather than in the preferred digital fashion.

It will now be apparent that the regulation afforded by the structure described with reference to FIG. 1 depends on a computer algorithm programmed into the computer 38. Ideally the algorithm should be capable of interpreting requirements for insulin to the point where the subject's blood glucose concentration is maintained substantially constant at a level which is considered normal for the subject in question.

An algorithm has been developed which is a function of both the blood glucose concentration (BG) determined by the analyser 32 and also a function of the rate of change of blood glucose concentration (ḂG). This rate of change is determined by averaging each signal received by the computer over a fixed time interval and computing on a weighted scale the differences between the previous 4 or 5 such averaged interval signals received by the computer. This weighting is illustrated in FIG. 2 in which serial values of slope are weighted in the equation:

$$\dot{BG} \text{ (average)} = \frac{\dot{BG}_{ab} + 2\dot{BG}_{bc} + 3\dot{BG}_{cd} + 4\dot{BG}_{de}}{10}$$

where the suffixes ab, bc, cd, de refer to serial values of ḂG between the respective points a, b, c, d and e. The last reading (i.e. BGde) is weighted greater than the others because this reading is the last taken and gives a greater indication of the direction the slope of the curves is taking.

Because the readings of BG are taken at frequent intervals, i.e. many times a second, the computer is aware of changes in blood glucose concentration as soon as the analyser 32, recorder 34, and converter 36 have had time to initially analyse the concentration and feed the signals to the computer 38. Averaging is necessary to minimize noise and other rapid variations which would otherwise distort the computed value of BG. The computer will act relatively quickly to cause the insulin to be pumped to the subject. However, it will be appreciated that the computer is always slightly behind the actual insulin requirements. The algorithm not only answers a requirement which may be several minutes old but also attempts to anticipate the absolute requirement at the time when the insulin is to be infused. This anticipation is partly dependant upon a difference factor (DF) which is part of the following relationship:

$$PBG = BG + DF \qquad (1)$$

where PBG is the projected blood glucose concentration anticipated, and BG is the blood glucose concentration read by the computer.

The difference factor (DF) is related to the rate of change of blood glucose concentration (ḂG) as follows:

$$DF = f_1(\dot{BG}) \qquad (2)$$

where ḂG is determined by the computer which compares an interval averaged reading of blood-glucose concentration with previous readings.

The function $f_1$ must be generally monotonic in shape and symmetric about the origin in the first and third quadrants. (The term "monotonic" is used in the context to describe a curve having no slope reversal along its length, although the slope may be zero at one or more points on the curve). In the first quadrant, the slope must be small (or 0) near the origin and be larger for larger values of ḂG. Exemplary monotonic waves of the required form are shown in FIGS. 3, 4, and 5. These waves are typical of many curves which could be satisfactory in use to determine a rate dependent difference factor for use in computing a projected blood glucose concentration as will now be described.

The actual rate (RI) of insulin pumped to the subject is a function of the difference factor DF and the blood glucose concentration BG. Consequently, because of the relationship shown in equation (1), the function can be stated as follows:

$$RI = f_2(PBG) \qquad (3)$$

The function $f_2$ must be generally sigmoidal in shape, i.e. it must have smaller slopes (or zero slope) at lower values of the projected blood glucose concentration PBG, a maximum finite slope at an intermediate value of PBG and with a subsequent smaller slope (or zero slope) at higher values of PBG. Sample sigmoidal curves are shown in FIGS. 6 to 8 and these are typical of many various curves of this type which would be satisfactory in use to determine the rate of insulin infusion RI from values of the projected blood glucose concentration PBG.

Three examples of the use of the artificial beta cell will be described. Of these examples, the first two involve normal dogs which were subsequently pancreatectomized to render them diabetic, and a third is a two day study on a human patient who had been pancreatectomized in the process of surgery for stomach cancer.

In these trials, the difference factor was expressed as follows:

$$DF = K1\dot{BG}^3 + K2\dot{BG} \qquad (4)$$

where K1 and K2 are constants chosen to adjust the magnitude of the difference factor and selected to establish its sensitivity to variations in the rate of change of blood glucose concentration. The difference factor DF shown in equation (4) was combined with equation (1) to determine the projected blood glucose concentration PBG and inserted into the following equation which relates the rate of insulin infusion RI to the projected blood glucose concentration PBG and therefore by way of the difference factor DF to the rate of change of blood glucose concentration ḂG.

$$RI = K3[1 + \text{Tanh}.K4(PBG - K5)] \qquad (5)$$

A similar equation can be used for the infusion of dextrose although no difference factor is involved. Such an equation is as follows:

$$RD = K6[1 - \text{Tanh}.K7(BG - K8)] \qquad (6)$$

The constants used in the equations were decided from a review of clinical data which includes the subject's body weight and daily insulin requirements together with previous experience gained in controlling blood glucose concentration. In general K3 is half the maximum required insulin infusion rate; K4 characterises the slope of the curve at which half maximum insulin infusion rate occurs; K5 is the blood glucose concentration at which half maximum insulin infusion rate occurs; and K6, K7 and K8 correspond respectively to K3, K4 and K5 but are related to dextrose rather than insulin.

The curves resulting from equations (4) and (5) and used on the animal subjects are shown in FIGS. 9 and 10. The curve in FIG. 9 indicates the relationship between the difference DF and the rate of change of blood glucose concentration ḂG while the curve in FIG. 10 indicates the relationship between the rate of insulin infusion RI and the projected blood glucose concentration PBG for the two animal subjects.

Reference is now made to FIG. 11 which shows the effects of a glucose loading test on a normal dog. It will be seen that during the period of the glucose loading, the glucose values reached a peak of 180 mg/100 ml. Subsequently, the blood glucose concentration dropped to approximately normal. At the same time, portal and peripheral immunoreactive insulin readings were plotted and these graphs also appear in FIG. 11.

Turning now to FIG. 12, this graph shows the same glucose loading test after the dog had been pancreatectomized. It will be seen that the glucose level after loading tended to remain at an elevated level with no indication that it would fall. After this test was completed, a further test was conducted on the dog using the artificial beta cell according to the invention. The results are shown in FIG. 13 in which it will be seen that the same glucose loading test resulted in a maximum glucose concentration of 130 mg/100 ml and that this concentration subsequently dropped to an acceptable level as a result of the peripheral insulin infusions. The peripheral immunoreactive insulin concentrations are also shown on this graph.

It will be seen from a comparison of FIGS. 12 and 13 that the artificial beta cell can not only restore the blood sugar concentration to normal in a surgically diabetic dog, but controls the maximum glucose concentration reached as a result of the loading test. The glucose loading test was chosen because it represents far more severe glucose tolerance testing than normally encountered in day-to-day life and in this way demonstrates that the artificial beta cell is more than capable of restoring blood sugar concentrations in a severely diabetic subject.

A further important aspect of the control achieved and demonstrated in FIG. 13, is that the drop in glucose concentration achieved after the loading test was discontinued, is also controlled. Consequently, hypoglycaemia does not result from the large rates of insulin infusion used to counteract the glucose loading. This is because of the shape of the graph used in relating the difference factor to the rate of change of blood glucose. Once the loading test is discontinued, BG becomes negative and the difference factor also becomes negative. Further, if BG becomes negatively large, then the form of the graph in the third quadrant is such that the difference factor also becomes negatively large. Consequently, the rate of infusion on the sigmoidal relationship with projected blood glucose (PBG) drops markedly and limits the possibility of the blood glucose level being driven down causing hypoglycaemia.

Reference is now made to FIGS. 14 and 15 which illustrate tests on a second dog. Graphs in FIGS. 14 and 15 correspond to graphs described with reference to FIGS. 11 and 13 and it will be seen that similar results were achieved. Here again, the maximum blood glucose concentration was smaller after pancreatectomy using the present apparatus than it was in the normal dog.

Reference is now made to FIG. 16 which illustrates parallel curves relating the rate of insulin infusion RI to the projected blood glucose concentration PBG. These curves and the curve of FIG. 8 were used in treating a human patient and the results obtained are shown in FIGS. 17 and 18. The reason for two curves is that initially, the curve to the left in FIG. 16 was used and it was found that the resulting blood glucose level tended to be lower than was required. Accordingly, because this patient was in serious need of treatment, the position of the curve was simply moved along the abscissa to increase the values of PBG. This was done by entering a new value of K5 in equation 5 via the typewriter 40 in FIG. 1. Accordingly, it will be seen in FIG. 17 that an initial dip in blood glucose concentration was corrected and this was the result of moving the curve in FIG. 16. Subsequently, the blood glucose concentration was stabilized in FIG. 17 as insulin was infused as a result of demands caused by treatment of the patient.

In FIG. 18, graphs were drawn for the same patient on the day subsequent to the graphs plotted in FIG. 17. In FIG. 18 the patient demonstrated an initial insulin resistance, fever, and required almost 70 units of insulin to restore normal blood glucose concentrations after which normoglycaemia was maintained with physiological amounts of insulin. Through the use of the artificial beta cell on this patient, a clear indication was obtained on two consecutive days of what was the precise amount of insulin required by the patient to maintain normal blood sugar levels during hyperalimentation. These results were of clinical benefit to the patient.

FIGS. 17 and 18 illustrate the fine regulation of blood glucose concentration achieved by the artificial beta cell applied to a diabetic human subject. It is anticipated that such results could be obtained consistently and for this reason the use of a dextrose system is considered unnecessary. However, it should be pointed out in the test on the human paitient, a back-up dextrose system was used for the sake of safety. The system is indicated in ghost outline in FIG. 1 and had similar components to that of the insulin system for infusing dextrose to the subject so that in the event that the blood glucose concentration fell below an acceptable level, dextrose could be administered. The delicate control achieved with the present apparatus eliminates the need for dextrose although for the sake of caution it may be more acceptable to include a dextrose system which can be used if necessary. Nevertheless, it is important to appreciate that very acceptable results have been achieved without reliance on a dextrose system to prevent hypoglycaemia.

It will be evident that various modifications can be made to the apparatus and method without departing from the invention. For instance analyzer 32 (FIG. 1) could be replaced by a glucose electrode sampling blood or tissue glucose. In this case the pump 28 and catheter 22 would not be needed and signals from the electrode would pass directly to the analog-to-digital converter 36.

A modification could also be made to the form of the weighting used to obtain an average value of BG. In this respect the weighting described has been found acceptable but is nevertheless typical of many conventional weighting techniques.

FIGS. 19 to 21 have been added to further illustrate exemplary curves which would be suitable as alternatives to the curves shown in FIGS. 3 to 5. It will be evident from the foregoing that many curves will be satisfacory if they are both monotonic and of reduced slope near the origin relative to larger slopes remote from the origin in both the first and third quadrants. Consequently, many curves can be used including for example curves having a first quadrant from any one of FIGS. 3 to 5 and a third quadrant from any one of the remaining Figs. Examples are shown in FIGS. 19 to 21 as typical of such suitable curves.

In general the function $f_1$ must be generally monotonic in shape and lie in the first and third quadrants. The slope must be small (or 0) near the origin and be larger for larger values of BG both positive and negative. All of the curves shown in FIGS. 3 to 5 and 19 to 21 satisfy these requirements and are exemplary of many such monotonic curves.

What we claim as our invention is:
1. An artificial beta cell comprising:
   blood analysis means for determining serial values of blood glucose concentration in the blood (BG) and including signal means for providing input signals corresponding to said values;
   means coupled to the blood analysis means to receive said input signals and including, first means for deriving serial values of the rate of change of blood glucose concentration in the blood (BG), second means receiving said values of BG and deriving a difference factor (DF) in accordance with a function of BG which is monotonic and symmetrical in the first and third quadrants, and has a slope which is never negative and which is smaller adjacent the origin than it is remote from the origin, and third means receiving DF and adding corresponding values of DF and BG to give a projected blood glucose concentration (PBG), and fourth means for deriving a desired rate of insulin infusion (RI) using the derived value of PBG from a sigmoidal relationship between PBG and RI and providing an output signal corresponding to the desired value of RI; and
   pump means coupled to receive the output signal and responsive to the output signal to supply the desired rate of insulin infusion to the subject.

* * * * *